United States Patent
Montessoro et al.

(10) Patent No.: US 6,399,836 B2
(45) Date of Patent: *Jun. 4, 2002

(54) PREPARATION OF DI-TERTIARY-PEROXIDES

(75) Inventors: Ezio Montessoro; Michele Merenda, both of Alessandria (IT)

(73) Assignee: ELF Atochem S.r.l., Milan (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/323,845

(22) Filed: Jun. 2, 1999

(30) Foreign Application Priority Data

Jun. 4, 1998 (IT) .......................... MI98A1250

(51) Int. Cl.$^7$ ............................. C07C 409/16
(52) U.S. Cl. ...................... 568/578; 568/558
(58) Field of Search ................. 568/558, 578

(56) References Cited

U.S. PATENT DOCUMENTS

| | | | |
|---|---|---|---|
| 2,403,758 A | | 7/1946 | Rust et al. |
| 2,668,180 A | * | 2/1954 | Boardman ................ 568/578 |
| 3,337,639 A | * | 8/1967 | Stedehouder et al. |
| 3,584,057 A | | 6/1971 | Schappell |
| 4,413,148 A | | 11/1983 | Kato et al. |
| 5,289,688 A | * | 3/1994 | Agrawal ..................... 62/651 |

FOREIGN PATENT DOCUMENTS

| | | | |
|---|---|---|---|
| GB | 896813 | * | 5/1962 |
| NL | 896813 | | 2/1960 |

* cited by examiner

Primary Examiner—Jean F. Vollano
(74) Attorney, Agent, or Firm—Arent Fox Kintner Plotkin & Kahn

(57) ABSTRACT

A process for the di-tertiary-peroxide synthesis, wherein the condensation reaction between a tertiary hydroperoxide and a tertiary alcohol is carried out in the presence of an acid catalyst, constituted by a compound having a monosulphonated aromatic ring selected from the following formulae:

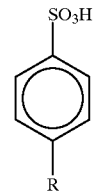

(I)

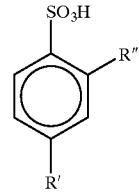

(II)

wherein: R is an alkyl group having from 2 to 9 carbon atoms, preferably from 2 to 6; R' and R'' are alkyl groups having a number of from 1 to 9 carbon atoms, preferably from 1 to 6.

15 Claims, No Drawings

PREPARATION OF DI-TERTIARY-PEROXIDES

The present invention relates to a process for preparing di-tertiary-peroxides, derived from the cumene hydroperoxide.

More specifically the present invention allows to have improved yields in the dicumylperoxide preparation process.

The condensation reaction between cumene hydroperoxide and alcohols with formation of di-tertiary-alkyl-aryl peroxides in the presence of acids as catalysts, is known in the prior art. Specifically, for the dicumyl peroxide preparation, cumene hydroperoxide and α-cumyl alcohol in the presence of more or less strong acid as catalysts are used.

The following processes for the dicumylperoxide production starting from cumene hydroperoxide and α-cumyl alcohol are known in the prior art.

Processes wherein a strong acid as sulphuric acid, methionic acid, toluene sulphonic acid, is used as catalyst in the reaction system. Other processes in which the same acids are used as catalysts and in which water is removed from the reaction mixture by distillation at reduced pressure and/or by addition of a volatile inert organic liquid (see G.B. 896,813).

Another process wherein as catalyst a strong acid of the above mentioned type is used, characterized in that the reaction is carried out in the presence of one or more polar solvents and the water formed during the reaction is continuously removed from the reaction system (see U.S. Pat. No. 4,413,148).

In another process oxalic anhydride is used in the reaction as acid catalyst and dehydrating agent (see U.S. Pat. No. 4,413,148).

Finally a process wherein a weak acid as potassium bi-sulphate is used as catalyst and wherein an inactive gas is continuously fed in the reaction system (see U.S. Pat. No. 4,413,148).

When a strong acid is used as catalyst the reaction must be carried out under restrictive conditions since both cumene hydroperoxide and dicumylperoxide are easily decomposed by the strong acid and it is necessary to select in an optimal way both the catalyst use amount and the reaction temperature; in general under the reaction conditions used in the above mentioned patents of the prior art, the process gives rather low yields.

Other meaningful drawbacks connected to the use of acid catalysts of the prior art in this process are the production of meaningful amounts of by-products and the reaction control difficulties and consequent safety problems.

The acid catalysts used in the prior art comprise both inorganic acids such as sulphuric acid, hydrochloric acid, perchloric acid and the like, and organic acids, such as para toluen sulphonic acid, methionic acid, trichloroacetic acid and the like.

One of the technical problems derived from the use of the sulphuric acid is the production of meaningful amounts of by-products, such as phenol, acetone, α methyl styrene, dimers of the α methyl styrene and others, with low yields and safety problems.

The use of the para-toluensulphonic acid shows advantages with respect to the sulphuric acid, improving the reaction yields and giving rise to a more controllable reaction.

The Applicant has surprisingly found a process to produce di-tertiary-peroxides, specifically dicumylperoxide, by reacting a tertiary-hydroperoxide with a tertiary-alcohol in the presence of a specific catalyst which allows, compared with the acid catalysts of the prior art, to further improve the reaction yields, by a by-product reduction.

It is therefore an object of the present invention a process for the synthesis of di-tertiary-peroxides, specifically dicumylperoxide, wherein the condensation reaction between a tertiary-hydroperoxide and a ter-alcohol is carried out in the presence of an acid catalyst, formed of a compound having a mono-sulphonated aromatic ring selected from the following formulae:

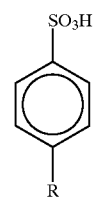

(I)

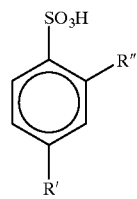

(II)

wherein: R is an alkyl group having from 2 to 9 carbon atoms, preferably from 2 to 6; R' and R" are alkyl groups having from 1 to 9 carbon atoms, preferably from 1 to 6.

Preferably the molar ratio between the tertiry-hydroperoxide and the tertiary-alcohol has a value in the range 0.9–1.2.

The acid catalyst is used in a percentage by weight in the range 10%–40% with respect to the reacting organic mixture.

The reaction can be carried out in a reactor wherein the acid catalyst of the present invention is gradually introduced inside the reaction system so that the reaction temperature is in the range 25°–60° C.

The reaction mass is maintained under stirring for about 30–90 minutes, at the end the acid aqueous phase is separated and the organic phase is recovered.

The product is characterized at the end of the condensation reaction, by gaschromatographic analysis (High Resolution Gas Chromatography HRGC) in order to evaluate the peroxide and the by-product content.

Subsequently the organic phase is washed with an alkaline solution to remove the phenol and the cumene hydroperoxide present in the reaction product. Then a washing is carried out with an aqueous solution to eliminate the residual alkalinity.

When the washings are over, the organic phase is subsequently purified by subjecting it to a stripping treatment in vapour counter-current to eliminate the volatile organic components.

At the end the product is anhydrified and characterized in terms of iodometric and gaschromatographic analysis titre with internal standard (titre higher than 98%).

Specifically the invention process is applicable for the dicumylperoxide preparation by reaction between cumene hydroperoxide and α-cumyl alcohol.

One of the main uses of the invention di-tertiary-peroxides is as polymer curing agent (e.g. PE, EPR etc.).

The present invention will be better illustrated by the following working examples, which have a merely indicative purpose but not limitative of the scope of the invention itself.

EXAMPLE 1 (COMPARATIVE)

In a standard glass reactor, of the automized Mettler RC1 calorimeter, 0.775 Kg of a mixture containing (% by weight) cumene hydroperoxide (CHP) 42.3%, α-cumyl alcohol (AC) 40.4% (ratio by weight 1.05) and cumene 17.3%, are introduced. At the temperature of 40° C., 0.145 Kg of para toluene sulphonic acid (APTS) at 65% by weight are added in 60 minutes. After the acid addition the reaction mass is maintained under stirring for one hour at the end of which the acid aqueous phase is separated. Subsequently the organic phase is washed with an alkaline solution and then with water obtaining 0.633 kg of organic phase at the washings end.

The HRGC analysis of the most important components, using as internal standard n-hexadecane (n-$C_{16}$), gives the results illustrated in Table 1:

TABLE 1

| Sample | Dicumyl Peroxide | α-methyl styrene | Phenol | AC | CHP |
|---|---|---|---|---|---|
| Reaction end | 69.9% | 5.6% | 5.4% | 2.6% | 0.17% |
| Washing end | 73.5% | 5.8% | absent | 2.8% | absent |

The condensation yield with respect to the α-cumyl alcohol is 74.9%.

The organic phase is subsequently purified by distillation in vapour counter-current and anhydrified, the final product having a iodometric titre 98.5%, gaschromatographic titre with internal standard 98.3%, is thus obtained.

EXAMPLE 2

Always in an automized Mettler RC1 calorimetric reactor, 0.775 Kg of the same mixture of cumene hydroperoxide (CHP) and α-cumyl alcohol (AC) in cumene used for Example 1, are introduced. At the temperature of 40° C., 0.145 Kg of cumen sulphonic acid (CUSA) at 65% by weight are added in 60 minutes. After the acid addition the reaction mass is maintained under stirring for one hour at the end of which the acid aqueous phase is separated. Subsequently the organic phase is washed as in the preceding Example. 0.636 kg of washed organic phase are obtained.

The HRGC analysis of the most important components, using the internal standard of Example 1, gives the results illustrated in Table 2:

TABLE 2

| Sample | Dicumyl Peroxide | α-methyl styrene | Phenol | AC | CHP |
|---|---|---|---|---|---|
| Reaction end | 73.1% | 3.4% | 4.5% | 2.8% | 0.4% |
| Washing end | 76.8% | 3.6% | absent | 2.9% | absent |

The condensation yield with respect to the α-cumyl alcohol is 78.7%.

The organic phase is subsequently purified as in the preceding Example; the final product having an iodometric titre 98.65%, gaschromatographic titre with internal standard of Example 1 equal to 98.4%, is thus obtained.

EXAMPLE 3

In the reactor used for the previous tests, 0.775 Kg of the same mixture of cumene hydroperoxide (CHP) and α-cumyl alcohol (AC) in cumene used for the previous tests are introduced. At the temperature of 40° C., 0.145 Kg of xylene sulphonic acid (XSA) at 65% by weight are added in 60 minutes. One proceeds as in the previous Examples and at the end of the washings 0.637 Kg of organic phase are obtained.

The HRGC analysis of the most important components, using the internal standard of Example 1, gives the results illustrated in Table 3:

TABLE 3

| Sample | Dicumyl Peroxide | α-methyl styrene | Phenol | AC | CHP |
|---|---|---|---|---|---|
| Reaction end | 71.9% | 5.0% | 5.3% | 2.4% | 0.3% |
| Washing end | 74.8% | 5.1% | absent | 2.9% | absent |

The condensation yield with respect to the α-cumyl alcohol is 76.7%.

The organic phase is subsequently purified as in the preceding Examples; a final product having an iodometric titre 98.4%, gaschromatographic titre with internal standard of Example 1 equal to 98.2%, is thus obtained.

EXAMPLE 4 (COMPARATIVE)

In the reactor used for the previous tests, 0.775 Kg of the same mixture of cumene hydroperoxide (CHP) and α-cumyl alcohol (AC) in cumene used for the previous tests are introduced. At the temperature of 45° C., 0.145 Kg of para toluene sulphonic acid (APTS) at 65% by weight are added in 60 minutes. One proceeds as in the previous Examples and at the end of the washings 0.630 Kg of organic phase are obtained.

The HRGC analysis of the most important components, using the internal standard of Example 1, gives the results illustrated in Table 4:

TABLE 4

| Sample | Dicumyl Peroxide | α-methyl styrene | Phenol | AC | CHP |
|---|---|---|---|---|---|
| Reaction end | 69.7% | 6.4% | 5.4% | 1.7% | 0.05% |
| Washing end | 72.9% | 6.6% | absent | 1.9% | absent |

The condensation yield with respect to the α-cumyl alcohol is 73.9%.

The organic phase is subsequently purified as in the preceding Examples; a final product having an iodometric titre 98.5%, gaschromatographic titre with internal standard of Example 1 equal to 98.3%, is thus obtained.

EXAMPLE 5

In the reactor used for the previous tests, 0.775 Kg of the same mixture of cumene hydroperoxide (CHP) and α-cumyl alcohol (AC) in cumene used for the previous tests are introduced. At the temperature of 45° C., 0.145 Kg of cumen sulphonic acid (CUSA) at 65% by weight are added in 60 minutes. One proceeds as in the previous Examples and at the end of the washings 0.630 Kg of organic phase are obtained.

The HRGC analysis of the most important components, using the internal standard of Example 1, gives the results illustrated in Table 5:

TABLE 5

| Sample | Dicumyl Peroxide | α-methyl styrene | Phenol | AC | CHP |
|---|---|---|---|---|---|
| Reaction end | 74.1% | 4.5% | 4.9% | 1.4% | 0.03% |
| Washing end | 77.0% | 4.7% | absent | 1.7% | absent |

The condensation yield with respect to the α-cumyl alcohol is 78.1%.

The organic phase is subsequently purified as in the preceding Examples; a final product having an iodometric titre 98.3%, gaschromatographic titre with internal standard of Example 1 equal to 98.3%, is thus obtained.

EXAMPLE 6

In the reactor used for the previous tests, 0.775 Kg of the same mixture of cumene hydroperoxide (CHP) and α-cumyl alcohol (AC) are introduced in cumene used for the previous tests. At the temperature of 45° C., 0.145 Kg of xylene sulphonic acid (XSA) at 65% by weight are added in 60 minutes. One proceeds as in the previous examples and at the end of the washings 0.637 Kg of organic phase are obtained.

The HRGC analysis of the most important components, using the internal standard of Example 1, gives the results illustrated in Table 6:

TABLE 6

| Sample | Dicumyl Peroxide | α-methyl styrene | Phenol | AC | CHP |
|---|---|---|---|---|---|
| Reaction end | 71.0% | 6.2% | 5.2% | 1.8% | 0.04% |
| Washsing end | 74.5% | 6.4% | absent | 2.0% | absent |

The condensation yield with respect to the α-cumyl alcohol is 76.4%.

The organic phase is subsequently purified as in the preceding Examples; a final product having an iodometric titre 98.3%, gaschromatographic titre with internal standard of Example 1 equal to 98.2%, is thus obtained.

From the analysis of the Examples and of the corresponding summarizing Table 7 it is noticed that the use of acid catalysts of formula (I) and (II) according to the invention leads to a notable improvement of the condensation yield in dicumylperoxide in comparison with the use of para toluen sulphonic acid (comparative Examples 1 and 4).

TABLE 7

| | Catalyst | Reaction temperature | Condensation yield | Final product titer |
|---|---|---|---|---|
| Example 1 (comp.) | APTS | 40° C. | 74.9% | 98.3% |
| Example 2 | CUSA | 40° C. | 78.7% | 98.4% |
| Example 3 | XSA | 40° C. | 76.7% | 98.2% |
| Example 4 (comp.) | APTS | 40° C. | 73.9% | 98.3% |
| Example 5 | CUSA | 40° C. | 78.1% | 98.3% |

TABLE 7-continued

| | Catalyst | Reaction temperature | Condensation yield | Final product titer |
|---|---|---|---|---|
| Example 6 | XSA | 40° C. | 76.4% | 98.2% |

What is claimed is:

1. A process for the synthesis of di-tertiary cumene peroxides comprising:

combining a tertiary cumene hydroperoxide and a tertiary alcohol in the presence of an acid catalyst within a temperature range of 25° C.–60° C., wherein the catalyst is at a concentration of from 10 to 40% by weight of the total concentration for the tertiary hydroperoxide, the tertiary alcohol and the acid catalyst, and the catalyst is a compound having a mono-sulphonated aromatic ring of formula

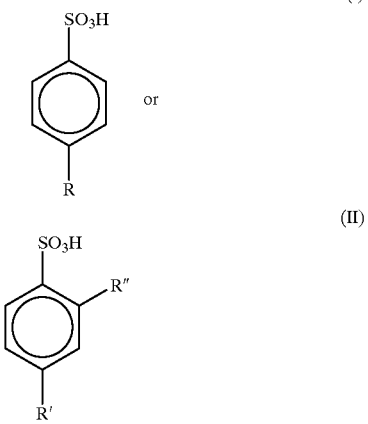

wherein:
R is a C2–C9 alkylic group;
R' and R" are C2–C9 alkyl groups;
stirring for 30–90 minutes, forming an acid aqueous phase and an organic phase, and thereafter separating the acid aqueous phase from the organic phase.

2. A process according to claim 1, wherein the molar ratio between the tertiary-hydroperoxide and the tertiary-alcohol has a value in the range 0.9–1.2.

3. A process according to claim 1, wherein at the end of the condensation reaction a washing step is carried out with an alkaline solution and subsequently with an aqueous solution.

4. A process according to claim 1, wherein R is an alkyl group having from 2 to 6 atoms, and R' and R" are alkyl groups having from 1 to 6 carbon atoms.

5. A process according to claim 1, wherein after the washing step, a purification step is carried out by a vapour counter-current stripping treatment to eliminate the volatile organic components.

6. A process according to claim 2, wherein at the end of the condensation reaction, a washing step is carried out with an alkaline solution and subsequently with an aqueous solution.

7. A process according to claim 4, wherein at the end of the condensation reaction, a washing step is carried out with an alkaline solution and subsequently with an aqueous solution.

8. A process according to claim 3, wherein an organic phase is recovered.

9. A process according to claim 2, for preparing by reacting cumene hydroperoxide and α-cumyl alcohol.

10. A process according to claim 1, for preparing ditertiary cumyl peroxide by reacting tertiary cumene hydroperoxide and α-cumyl alcohol.

11. A process according to claim 3, for preparing ditertiary cumyl peroxide by reacting tertiary cumene hydroperoxide and α-cumyl alcohol.

12. A process according to claim 4, for preparing ditertiary cumyl peroxide by reacting tertiary cumene hydroperoxide and α-cumyl alcohol.

13. A process according to claim 2, wherein after the washing step, a purification step is carried out by a vapour counter-current stripping treatment to eliminate volatile organic compounds.

14. A process according to claim 3, wherein after the washing step, a purification step is carried out by a vapour counter-current stripping treatment to eliminate volatile organic compounds.

15. A process according to claim 4, wherein after the washing step, a purification step is carried out by a vapour counter-current stripping treatment to eliminate volatile organic compounds.

* * * * *